United States Patent [19]

Folkers et al.

[11] Patent Number: 5,316,765

[45] Date of Patent: * May 31, 1994

[54] USE OF COENZYME Q$_{10}$ IN COMBINATION WITH HMG-COA REDUCTASE INHIBITOR THERAPIES

[75] Inventors: Karl A. Folkers, Austin; Per H. Langsjoen, Temple; Richard A. Willis, Austin, all of Tex.

[73] Assignee: Karl Folkers Foundation for Biomedical and Clinical Research, Austin, Tex.

[*] Notice: The portion of the term of this patent subsequent to Jan. 21, 2009 has been disclaimed.

[21] Appl. No.: 762,312

[22] Filed: Sep. 19, 1991

Related U.S. Application Data

[63] Continuation-in-part of Ser. No. 404,228, Sep. 7, 1989, Pat. No. 5,082,650.

[51] Int. Cl.$^5$ .................. A61K 45/00; A61K 31/405; A61K 31/35; A61K 31/12
[52] U.S. Cl. ................................. 424/94.1; 514/415; 514/460; 514/690; 514/922
[58] Field of Search ............... 424/94.1; 514/415, 460, 514/510, 689

[56] References Cited

U.S. PATENT DOCUMENTS

| | | | |
|---|---|---|---|
| 4,231,938 | 11/1980 | Monaghan et al. | 549/292 |
| 4,346,227 | 8/1982 | Terahara et al. | 560/119 |
| 4,444,784 | 4/1984 | Hoffman et al. | 514/460 |
| 4,824,669 | 4/1989 | Folkers et al. | 424/94.1 |
| 4,885,167 | 12/1989 | Folkers et al. | 424/94.1 |
| 4,929,437 | 5/1990 | Tobert | 424/10 |
| 4,933,165 | 6/1990 | Brown | 424/10 |
| 5,082,650 | 1/1992 | Folkers et al. | 424/10 |

OTHER PUBLICATIONS

Alberts et al., (1980), *Proc. Natl. Acad. Sci. USA*, 77:3957–3961.
Crane, F. L., (1986), *Biomedical and Clinical Aspects of Coenzyme Q*, K. Folkers and Y. Yamamura, Eds., Amsterdam, The Netherlands: Elsevier Science Publishers, B. V., 5:3–14.
Endo et al., (1976), *F.E.B.S. Lett.*, 72:323–326.
Goodman and Gilman, eds., (1989), In: *The Pharmacological Basis of Therapeutics*, 7th edition, MacMillan Publishing Co., New York, N.Y. pp. 841–845.
Budavari et al., eds., (1989), In: *The Merck Index*, 11th edition, Merck and Co., Inc. Publishers, p. 1222.
Langsjoen et al., (1988), *Klinische Wochenschrift*, 66:583–590.
Langsjoen et al., (1990), *The American Journal of Cardiology*, 65:521–523.
Balasubramanian, N., et al., (1989), *J. Med. Chem.*, 32:2038–2041.
Roth, B. D. et al., (1991), *J. Med. Chem.*, 34:357–366.
Krause, R. et al., (1990), *J. Drug Dev.*, 3(1): 255–257.
Karanewsky, D. S. et al., (1990), *J. Med. Chem.* 33:2952–2956.
Folkers et al., (1985), *Proc. Natl. Acad. Sci., USA*, 82:901.

(List continued on next page.)

*Primary Examiner*—Douglas W. Robinson
*Assistant Examiner*—Jean C. Witz
*Attorney, Agent, or Firm*—Arnold, White & Durkee

[57] ABSTRACT

Disclosed are methods for inhibiting the side effects attendant treatment with HMG-CoA reductase inhibitors. Treatment of a patient with and HMG-CoA reductase inhibitor in combination with coenzyme Q$_{10}$ provides a reduction in patient cholesterol levels and guards against typical HMG-CoA reductase-inhibitor side effects, most notably liver dysfunction and cardiac dysfunction. The combination of lovastatin, an HMG-CoA reductase inhibitor, and coenzyme Q$_{10}$ in ratios of between 1:2 to 1:29 provide significant enhancement of a patient's cariadc condition. By way of example, other HMG-CoA reductase inhibitors which may be included in the claimed combinations include pravastatin, compactin, fluvastatin, dalvastatin, simvastatin, BMY 22089, GR-95030, HR-780, CI-981, SQ 33,600, and BMY 22566 and XU-62-320.

4 Claims, 2 Drawing Sheets

OTHER PUBLICATIONS

Merck, Sharp and Dohme, Publishers, (1988) Product Monograph of Mevacor® (Lovastatin/MSD), pp. 1–77.

Dr. Emile G. Bliznakov and Gerald L. Hunt, The Miracle Nutrient Coenzyme $Q_{10}$, Bantam Books, (1986), New York, N.Y., pp. 64–104, p. 123 and pp. 220–232.

Folkers, et al. (1985), *Proc. Natl. Acad. Sci., USA*, 82:4513–4516.

Willis, et al. (1990), *Proc. Natl. Acad. Sci., USA*, 87:8928–8930.

Folkers, et al, (1990), *Proc. Natl. Acad. Sci., USA*, 87:8931–8934.

Folkers et al., (1970), *Intnl. J. Vit. Nutr. Res.*, 40:380–390.

Ganong, W. F., (1981), *In: Rev. Med. Phys.*, Los Altos, Lange Medical Publication, pp. 441–451.

Baker et al., (1981), *Elsevier/N.-Holland Biomedical Press*, 193–206.

Vadhanavikit et al., (1984), *Biochem. Biophys. Res. Commun.*, 123(3):1165–1169.

Mortensen et al., (1984), *Drugs Exptl. Clin. Res.*, (7):497–502.

Kubicek et al., (Dec. 1966), *Aerospace Med.*, pp. 1208–1212.

DePierre et al., (1977), *Ann. Rev. Biochem.*, 201–262.

Crane et al., (1957), *Biochem. Biophys. Acta.*, 25:220–221.

Saviotti et al., (1984), *G. Neuropsichiatr. Eta. Evol.*, 4/Suppl.1 (67–69), p. 337.

Venco et al., (1984), *G. Neuropsychiatr. Eta. Evol.*, 4//Suppl.1 (61–66), p. 341.

Carafoli et al., (1980), *Molec. Aspects of Med.*, 3:295–429.

Sunamori et al., (1984), *In Biomed. and Clin. Aspects of Coenzyme Q*, ed. Folkers et al., 4:333–342.

Michelson et al., (1955), *Proc. Natl. Acad. Sci.*, 41:1079–1084.

West, (1966), *Annals. N.Y. Accad. of Sciences*, 138:4–13.

Welsh et al., (1963), *Arch. Int. Med.*, 112:97–104.

Durnin et al., (1960), *J. Iowa Med. Soc.*, 59:113–115.

Morgan-Hughes, (1983), *In Advanced Med.*, ed. by Saunders, 19:243–260.

Farley et al., (1966), *Biochem. and Biophys. Res. Comm.*, 24:299–303.

Nilsson et al., (1968), *Arch. Biochem and Biophys.*, 133:422–426.

Lenaz et al., (1968), *Arch. Biochem. and Biophys.*, 123–539–550.

Scholler et al., (1968), *Int. J. for Vit. Res.*, 38:362–368.

Littarru et al., (1970), *Biochem. and Biophys. Res. Comm.*, 41:1306–1313.

Danowski et al., (1971), *Arch. of Physical Med. and Rehab.*, 52:193–200.

Sovik et al., (1971), *Acta Pediat. Scand.*, 60:428–432.

Zellweger et al., (1971), *Acta. Neurol. Scand.*, 48:87–101.

Folkers, et al., (1972), *Int. J. Vit. Nutr. Res.*, 42:139–163.

Griggs, (1974), *Circ. Res.*, 34 and 35, pp. II-145-II-150.

Folkers et al., (1974), *Proc. Natl. Acad. Sci., USA*, 71:2098–2101.

Kuhn et al., (1979), *Neurology*, 29:1144–1149.

Reeves et al., (1980), *Arch. Neurol.*, 37:273–277.

Hopkins et al., (1981), *Annals of Neurol.*, 10:230–237.

Kishi et al., (1981), *Biomed. and Clin. Aspects of Coenzyme Q*, vol. 3, Eds. Folkers et al., pp. 67–78.

Couch et al., (1981), ibid, pp. 257–266.

Folkers et al., (1981), ibid, pp. 399–412.

Goldberg et al., (1982), *Neurology*, 21:1101–1105.

Hawley et al., (1983), *Arch. Int. Med.*, 143:2134–2136.

Bender, (Jan. 1984), *Hospital Medicine*, pp. 95–125.

Morgan-Hughes et al., (1984), *Biomed. and Clin. Aspects of Coenzyme Q*, Elsevier Science Pub., 4:417–424.

Ho et al., (1975), Abstract.

USE OF COENZYME $Q_{10}$ IN COMBINATION WITH HMG-COA REDUCTASE INHIBITOR THERAPIES

The present application is a continuation-in-part of Applicants' co-pending U.S. patent application U.S. Ser. No. 07/404,228, filed Sep. 7, 1989 now U.S. Pat. No. 5,082,650.

BACKGROUND OF THE INVENTION

1. Field of the Invention

The field of the present invention relates to methods and compositions for reducing side effects HMG-CoA reductase inhibitor therapy particularly those related to the physiologically depressed levels of coenzyme $Q_{10}$ in the animal. Most particularly, the invention provides methods effective for the reduction of cholesterol using an HMG-CoA reductase inhibitor, while reducing and/or inhibiting the side effects clinically linked to the use of HMG-CoA reductase inhibitors, such as liver dysfunction, musculoskeletal, nervous system/psychiatric, cardiac dysfunction, skin and special senses disorders. The invention also provides specifically defined formulations which include a mixture of an HMG-CoA reductase inhibitor and coenzyme $Q_{10}$.

2. Description of the Related Art

Coronary artery disease is the major cause of death in Western countries. Hypercholesterolemia is known to be a primary risk factor for death from coronary artery disease. It is known that 50% or more of the total body cholesterol in humans is derived from intrinsic biosynthesis. It is also known that a rate-limiting step of major significance in the biosynthesis of cholesterol is at the level of the enzyme known as 3-hydroxy-3-methylglutaryl-coenzyme A reductase or HMG-CoA reductase. This enzyme then was logical for inhibition to reduce the intrinsic biosynthesis of cholesterol toward reducing the risk factor of hypercholesterolemia and coronary artery death.

Alberts et al. described the isolation, structure and biochemical properties of an active inhibitor of HGMCoA reductase which they named mevinolin. The scientific name, mevinolin, introduced in 1980, corresponds to the subsequent trademark name, MEVACOR®. This chemical substance is 1,2,6,7,8,8a-hexahydro-$\beta,\delta$-dihydroxy-2,6-dimethyl-8-(2-methyl-1-oxobutoxy)-1-naphthaleneheptanoic acid$\delta$-lactone.

The Product Monograph on lovastatin (i.e., mevinolin) by Merck, Sharp and Dohme (issued May 1988, DC 7,489,503) states that lovastatin is highly effective in the treatment of hypercholesterolemia. Further, at maximum doses, lovastatin produced a mean reduction of LDL cholesterol of 394 in two large multicenter control studies. In general, lovastatin was found to be well-tolerated in continuing extensive clinical trials as based on data from studies worldwide. Unfortunately, approximately 2% of patients were discontinued from therapy due to drug-related adverse effects in all clinical studies. The most frequently reported adverse side-effects were: headache (9.3%), flatus (6.4%), abdominal pain/cramps (5.7%), diarrhea (5.5%) and rash/pruritus (5.2%) (Id. at page 56).

Further, (Id.) the adverse experiences on treating patients with lovastatin in controlled clinical studies were GASTROINTESTINAL (constipation, diarrhea, dyspepsia, flatus, abdominal pain/cramps, heartburn and nausea); and MUSCULOSKELETAL (muscle cramps and myalgia); and NERVOUS SYSTEM/PSYCHIATRIC (dizziness, headache); SKIN (rash/pruritus); and SPECIAL SENSES (blurred vision and dysgeusia). Although some of these adverse experiences were also recorded when a placebo was administered, lovastatin consistently and definitely produced such adverse experience.

Also, (Id. at page 68), liver dysfunction from lovastatin can occur and approximately 0.5% of patients in clinical trials developed a myopathy.

Also, (page 68), there were eye dysfunctions indicated by a high prevalence of baseline lenticular opacities and during clinical trials, the appearance of new opacities was noted. The causal relationship of lovastatin to these opacities was not established. Of 431 patients, 34 had opacities at the final examination which occurred during 5–15 months after initiating therapy with lovastatin. However, existing opacities did not appear to increase.

In summary of the tolerability or the side effects from the clinical administration of lovastatin, this drug does have a variety of definite side effects some of which, particularly liver dysfunction, have justified discontinuation of therapy with lovastatin. Providing a method whereby the valuable group of HMG-CoA reductase inhibitors, such as lovastatin, could be used with a diminished risk for, or with the elimination of, the above-described physiological side effects, would provide a significant advance in the media acceptability and scope of treatable population for whom the use of such agents may be utilized.

SUMMARY OF THE INVENTION

The presently disclosed invention provides methods and compositions to be used in the prevention of a variety of HMG-CoA reductase inhibitor-related physiological side-effects. By way example, such side-effects include cardiac dysfunction, liver dysfunction, immune system function, headache, flatus, abdominal pain/cramps, diarrhea, rash-pruritus, and eye dysfunctions. Those eye dysfunctions observed most frequently in persons maintained on HMG-CoA reductase inhibitor therapy include baseline lenticular opacities.

More specifically, the present inventors utilize the heretofore overlooked and very serious side effect of HMG-CoA reductase inhibitors to depress body levels of Coenzyme $Q_{10}$. Depressed levels of serum coenzyme $Q_{10}$ have been found by the present inventors to correspond to an increased observed incidence of cardiac dysfunction or the decreased pumping of blood by the heart throughout the body. The present methods and formulations counteract the side effects commonly observed with the treatment of a patient with HMG-CoA reductase inhibitors. By supplementing the patient levels of coenzyme $Q_{10}$, such side effects are remedied or prevented.

One embodiment of the present invention, a formulation is provided which contains a concentration of an HMG-CoA reductase inhibitor and coenzyme $Q_{10}$ which is suitable for administration to patients to produce a clinically effective reduction of cholesterol while simultaneously maintaining physiologically protective levels of coenzyme $Q_{10}$. The pharmaceutical formulation of the present invention is found to be effective in maintaining clinically effective coenzyme $Q_{10}$ blood levels for normal cardiac function and in maintaining proper immune system function. As such, the present pharmaceutical formulation maintained within the body of a treated animal provides physiological protective levels of coenzyme $Q_{10}$.

The formulations of the present invention may be used in conjunction with virtually any of the family of those substances known as HMG-CoA reductase inhibitors. Those particular HMG-CoA reductase inhibitors most preferred for use in conjunction with the present formulation as selected from the group consisting of: simvastatin, lovastatin, pravastatin, compactin fluvastatin dalvastatin, HR-780, GR-95030, CI 980, B My 22089, and B My 22566. In particularly preferred embodiments of the present formulations, the HMG-CoA reductase inhibitor is pravastatin or lovastatin. In an even more particularly preferred embodiment, the formulation of the present invention includes the HMG-CoA reductase inhibitor is lovastatin.

As part of the claimed formulation, the HMG-CoA reductase inhibitor is included together with coenzyme $Q_{10}$ and clinically effective weight ratios of between 1:2 to 1:20. Even more particularly, the ratio of the HMG-CoA reductase inhibitor to coenzyme $Q_{10}$ in the formulation is between 1:5 to 1:10. The most preferred embodiment of the claimed formulations, the ratio of HMG-CoA reductase inhibitor, most particularly lovastatin, to coenzyme $Q_{10}$ is 1:10. The range of ratios of an HMG-CoA reductase inhibitor to coenzyme $Q_{10}$ described herein may be employed with virtually any HMG-CoA reductase inhibitor.

Where the particular HMG-CoA reductase inhibitor is pravastatin, the ratio of pravastatin to coenzyme $Q_{10}$ is preferably within the range 1:2 to 1:20, Wt/Wt. For example, pravastatin/coenzyme $Q_{10}$ at a ratio of 1:2 would include 40 mg/day pravastatin with 80 mg/day coenzyme $Q_{10}$. Where the ratio of pravastatin/coenzyme $Q_{10}$ is at a ratio of 1:20, for example, 20 mg/day pravastatin would be administered with 400 mg/day coenzyme $Q_{10}$. Even more particularly, the ratio of pravastatin to coenzyme $Q_{10}$ is within the range of 1:5 to 1:10. Even more preferably, the ratio of pravastatin to coenzyme $Q_{10}$ is 1:10 (Wt/Wt). For example, a formulation which includes a 1:10 ratio of pravastatin to coenzyme $Q_{10}$ is 20 mg/day pravastatin with 200 mg/day coenzyme $Q_{10}$. Weight ratio of ingredients described herein in regard to the HMG-CoA reductase inhibitors, lovastatin and provastatin are applicable for any HMG-CoA reductase inhibitor.

For the purposes of the present invention, the term physiologically protected levels in regard to the description of coenzyme $Q_{10}$ is more specifically defined as a blood serum level of coenzyme $Q_{10}$ of between 1.0 $\mu$g/ml and 5.0 $\mu$g/ml. Given more specifically, the term physiological protective levels as that term is used in regard to describing coenzyme $Q_{10}$ levels in a patient is defined as between 1.5 $\mu$g/ml and 3.5 $\mu$g/ml coenzyme $Q_{10}$. The most preferred embodiment of the described formulations and methods, the term physiologically protective levels of coenzyme $Q_{10}$ is defined as about 2.5 $\mu$g/ml (serum concentration).

Even more particularly, the presently disclosed formulations may be described in terms of their relative concentrations (grams) administered to the animal as part of a continuous daily and/or monthly regimen. In one particular embodiment, the formulation is administered so as to provide the patient with between 20–40 milligrams per day of the HMG-CoA reductase inhibitor (i.e., lovastatin) together with a daily dose of coenzyme $Q_{10}$ of between 100 to 200 mg per day. Most preferably, the HMG-CoA reductase inhibitor, such as lovastatin, is administered at a daily dose of about 20 mg per day together with a dose of about 200 mg per day coenzyme $Q_{10}$. This particular embodiment of the claimed formulation will maintain within the patient efficient levels of coenzyme $Q_{10}$ so as to protect against the various HMG-CoA reductase inhibitor of related side effects described supra.

One particularly preferred embodiment of the invention provides a method for treating physiological side effects of an HMG-CoA reductase inhibitor therapy in an animal. This method most preferably comprises administering coenzyme $Q_{10}$ at a concentration sufficient to raise serum levels of coenzyme $Q_{10}$ in the animal to at least 1.0 $\mu$g/ml. Even more preferably, coenzyme $Q_{10}$ administrated at concentrations sufficient to raise serum levels of coenzyme $Q_{10}$ in the animal to at least 2.0 $\mu$g/ml.

While the described methods and formulations are expected to guard against virtually all side effects incident an HMG-CoA reductase inhibitor therapy regimen, those most serious physiological side effects to which the present methods and formulations are directed, include liver dysfunction as well as cardiac dysfunction.

As part of the described method, a concentration of coenzyme $Q_{10}$ sufficient to raise serum levels of coenzyme $Q_{10}$ to at least 1.0 $\mu$g/ml is about 100 mg per day for at least 30 days. Still another embodiment of the described method, the concentration of coenzyme $Q_{10}$ found sufficient to raise serum levels of coenzyme $Q_{10}$ and in an animal to at least 2.0 $\mu$g/ml is at least about 200 mg per day coenzyme $Q_{10}$ for at least 30 days, administered in conjunction with the HMG-CoA reductase inhibitor. This method has been found to be particularly effective in guarding against the development of dangerously low and life-threatening concentrations of coenzyme $Q_{10}$ on patients being maintained on the HMG-CoA reductase inhibitor known as lovastatin.

As noted, the present invention comprises the heretofore overlooked and very serious side effect of lovastatin and other HMG-CoA reductase inhibitors for depressing body levels of coenzyme $Q_{10}$. Lowered coenzyme $Q_{10}$ levels have been found by the present inventors to result in a corresponding depression of cardiac function, or the pumping of blood by the heart throughout the body. Circumvention of this death-threatening side effect was found by the present inventors to exist in the clinical administration of a formulation of coenzyme $Q_{10}$ either (1) concomitantly with an HMG-CoA reductase inhibitor, such as melvinolin (i.e., lovastatin) or (2) by independent formulations of an HMG-CoA reductase inhibitor and coenzyme $Q_{10}$ by an appropriate dosage schedule for the selected HMG-CoA reductase inhibitor and coenzyme $Q_{10}$ ($CoQ_{10}$).

The depressed cardiac function which can be caused by the administration of an HMG-CoA reductase inhibitor, such as (melvinolin) lovastatin, has been correlated by the inventor with a reduction in blood levels of coenzyme $Q_{10}$ ($CoQ_{10}$).

Crane[2] reviewed the physiological function of coenzyme $Q_{10}$. $CoQ_{10}$ is a redox coenzyme of the respiratory chain including mechanisms of oxidative phosphorylation. These mechanisms have been known as "bioenergetics" and support life functions including the cardiac function or the pumping of blood by the heart. $CoQ_{10}$ is also an important coenzyme for the mitochondrial enzymes: NADH:$CoQ_{10}$ reductase, succinate:$CoQ_{10}$ reductase, electron transfer flavoprotein:$CoQ_{10}$ reductase, reduced $CoQ_{10}$:cytochrome C reductase.

The energy coupling roles of $CoQ_{10}$, and the antioxidant activity of $CoQ_{10}$, are the specific reactions which are important to maintain metabolic functions of organs such as cardiac function. A pharmacological treatment or a drug treatment including the clinical administration of an HMG-CoA reductase inhibitor, such as lovastatin (mevinolin) to reduce hypercholesterolemia is described by the present inventors to result in a concomitant reduction in blood levels of $CoQ_{10}$. This reduction in blood levels of $CoQ_{10}$ result in a reduction in the energy-coupling and other roles of $CoQ_{10}$ and is determined by the present inventors to be clinically detrimental even to the point of adversely affecting cardiac function and even life itself.

DETAILED DESCRIPTION OF THE PREFERRED EMBODIMENTS

Figure 1A:
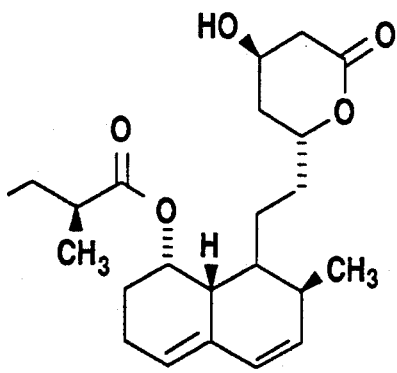
FIG. 1—CHEMICAL STRUCTURES OF HMG-CoA REDUCTASE INHIBITORS. The chemical structures of mevastatin (a.k.a. compactin), pravastatin, simvastatin, lovastatin, Bmy 22089, CI-981, SQ 33,600 and HR 780 are provided.
Figure 1B:
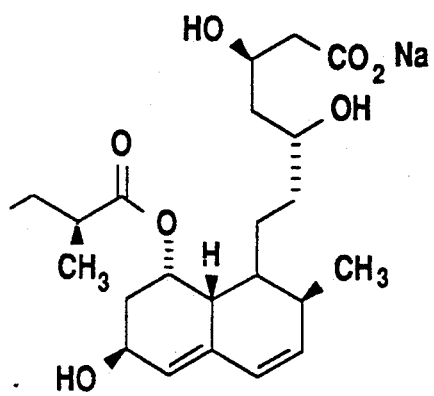
Figure 1C:
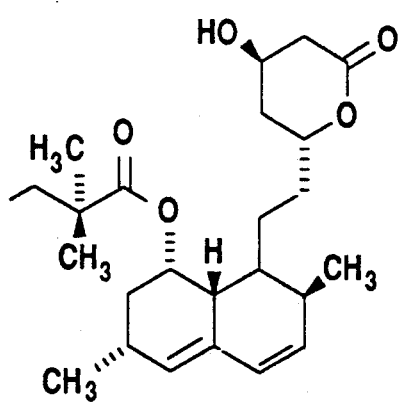
Figure 1D:
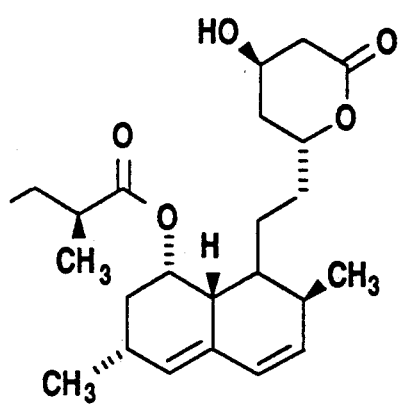
Figure 1E:
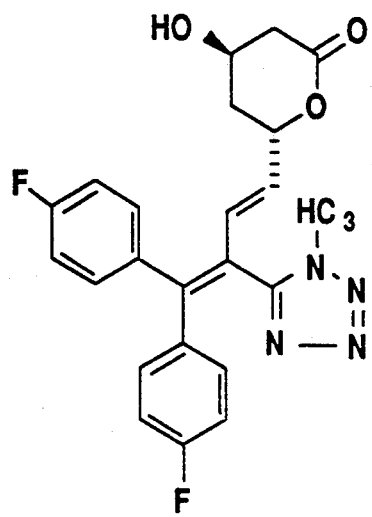
Figure 1F:
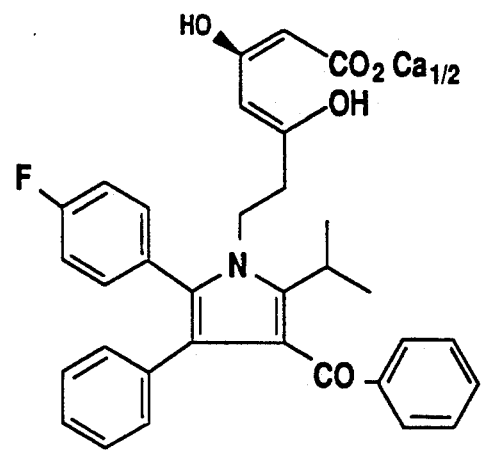
Figure 1G:
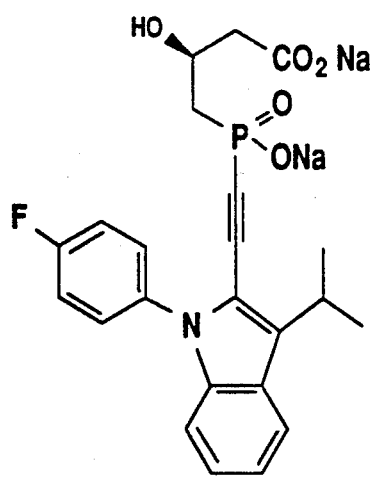
Figure 1H:
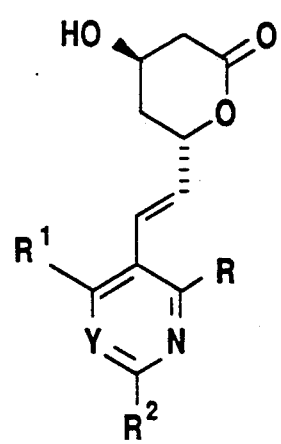

This invention relates to newly discovered methods and formulations to inhibit or counteract reductions in levels of coenzymes $Q_{10}$ in human subjects. Reduction in $CoQ_{10}$ is demonstrated by the present inventors to be a side effect of the administration of an HMG-CoA reductase inhibitor. The reduction of tissue levels of coenzyme $Q_{10}$ by oral administration of an HMG-CoA reductase inhibitor can in turn cause an increase in cardiac dysfunction, and for patients with advanced cardiac disease, this added dysfunction can be life-threatening.

Also, a reduction in levels of $CoQ_{10}$ in human subjects by an HMG-CoA reductase inhibitor, such as lovastatin or pravastatin, can depress other essential functions in the human body. By way of example, essential functions such as those of the immune system, can be very seriously affected, and even life-threatening, particularly in populations of persons who are already immunologically compromised, such as the cancer patient.

Various HMG-CoA reductase inhibitors, including lovastatin (mevinolin) are presently administered to countless patients all over the United States for the treatment of hypercholesterolemia. The data herein reveal that oral administration of an HMG-CoA reductase inhibitor, lovastatin, causes a reduction in the blood levels of coenzyme $Q_{10}$ in typical subjects. Perhaps more importantly, these data also demonstrates that this reduction of $CoQ_{10}$ is definitely related to a decrease in ejection fraction or an increase in cardiac dysfunction. It is also clearly evident scientifically that there would definitely be a decrease in immune function, as well as other metabolic functions, which are intrinsically dependent upon adequate tissue levels of coenzyme $Q_{10}$.

Many of the patients presently being treated in the U.S. with lovastatin have mild to severe stages of cardiomyopathy, dilated or ischemic, and ranging from mild cases to and including Class I to severe patients up to and including Class III and IV.

The classification of cardiac functional capacity as defined by the New York Heart Association is as follows:

Class I: Ordinary activity causes no discomfort.
Class II: Ordinary activity causes symptoms.
Class III: Minimal activity causes distress.
Class IV: Patient is symptomatic at rest.

Clinically, it is presently common for lovastatin to be administered to patients having hypercholesterolemia over prolonged periods of time ranging from weeks to months to years, and for the longer periods to prophylactically maintain low levels of cholesterol. This prolonged administration of lovastatin to a variety of patients definitely indicates that countless such patients will have depressed tissue levels of $CoQ_{10}$ and correspondingly depressed metabolic functions such as cardiac, immune, and others.

Patients presently receiving lovastatin have a great range of age, doubtless from the 20's to the 80's or even older. Such patients of such variable age will necessarily have variable levels of $CoQ_{10}$ according to present biochemistry, and thus their variable low tissue levels of $CoQ_{10}$ will bear some relationship to degrees of cardiac dysfunction, immunodysfunction, etc.

The case summaries and data described herein clearly illustrate that the administration of lovastatin to human subjects having from mild (Class I) to severe (Class IV) stages of cardiomyopathy can result in variable periods of time in reductions of $CoQ_{10}$ blood levels and such reductions are independently known to be correlated with degrees of cardiac dysfunction or cardiomyopathy, including both dilated and ischemic categories.

Of these case summaries, lovastatin caused such significant deterioration of cardiac function that a patient initially in Class II declined to Class IV with decompensation and chest pain which resulted in surgical revision of one graft.

In one of the described cases, lovastatin caused such rapid deterioration to a severe Class IV from an earlier Class III state that the patient was referred for a cardiac transplant. However, increasing the oral dosage of $CoQ_{10}$ to 200 mg daily circumvented the need for a cardiac transplant and allowed the patient to improve from a severe Class IV to a Class II.

These case summaries clearly illustrate the discovered severe side effect of lovastatin to depress $CoQ_{10}$ blood levels and to cause an increase to more severe NYHA (New York Heart Association) cardiomyopathy classifications whether the initial cardiac condition before treatment with lovastatin was Class I or Class II or Class III. This projection would be the same if the study were based on 50 cases or 100 cases or even more.

In cardiology, the treatment of patients having from mild to severe cardiomyopathy with lovastatin which has been shown herein to depress $CoQ_{10}$ blood levels and to depress cardiac function is clinically very undesirable because the quality of cardiac function is depressed and even a life-threatening status can develop which may require surgery and even a cardiac transplant.

The following examples are intended to describe the best mode and preferred embodiments of the present invention and are not intended to limit the claims unless otherwise specified.

EXAMPLE 1

Therapeutic Preparations of RNG-CoA Reductass Inhibitors and $CoQ_{10}$

The present example is presented to provide examples of those HMG-CoA reductase inhibitors which are included within the scope of the present invention. Compositions which include the listed HMG-CoA reductase inhibitors, as well as other compounds, are useful in the reduction and/or inhibition of side effects attendant the use of an HMG-CoA reductase inhibitor.

The term used to describe the class of chemical substances which cause a reduction in coenzyme $Q_{10}$ are the HMG-CoA reductase inhibitors.

By way of example, Table 1 presents a listing of several inhibitors of HMG-CoA reductase. These substances vary in their potency in their abilities to inhibit in HMG-CoA and also in their ability to reduce and/or inhibit coenzyme $Q_{10}$ levels.

HMG-CoA reductase inhibitor-associated side effects from depressed levels of $Q_{10}$ may be controlled via co-administration with a HMG-CoA reductase inhibitor of choice, or through administration of coenzyme $Q_{10}$ alone.

TABLE 1

Simvastatin
Lovastatin
Pravastatin
Compactin (a.k.a., mevastatin)
Fluvastatin
Dalvastatin
GR-95030
HR-780
SQ 33,600
B My 22089
B My 22566
CI 981

The HMG-CoA reductase inhibitors of the present invention are also characterized by an ability to stimulate receptor-mediated clearance of hepatic low-density lipoproteins (LDL), as an antihypercholesterolemic, and as a competitive inhibitor of HMG-CoA reductase.

The HMG-CoA reductase inhibitor employed may be lovastatin, sinvastatin, pravastatin, XU-62-320 (Sodium 3.5-dihydroxy-7 [3-(4-fluorophenyl)-1(methylethyl)-IH-Indole-2yl]-hept-6-enoate), mevastatin (a.k.a., compactin), BNY 22089, CI-981, SQ 33,600, HR 78OBMY 22089, CI 981, HR 780, SQ 33,600 or any other member of the class of compounds that inhibit HMG-CoA reductase. The preparation of lovastatin,[4] simvastatin,[5] and pravastatin[6] have been described in the patent literature. The preparation of XU-62-320 (fluvastatin) is described in WIPO Patent W084/02131. BMY 22089(13), CI 981(14), HR 780(15), and SQ 33,600(16) are also described in the literature cited, and are specifically incorporated herein by reference for the purpose of even more fully describing the chemical structure and synthesis of these HMG-CoA reductase inhibitors. These methods of preparation are hereby incorporated by reference.

Coenzyme $Q_{10}$ is manufactured by the Kanegafuchi Chemical Industry Co., Ltd. and is widely available.

Also within the scope of those HMG-CoA reductase inhibitors of the present invention are included the bioactive metabolites of those compounds listed in Table 1, such as pravastatin sodium[8] (the bioactive metabolite of mevastatin).

Any one or several of those HMG-CoA reductase inhibitor compounds listed in Table 1 may be formulated together with $CoQ_{10}$ to provide a therapeutically effective treatment for a patient, without the attendant risk of reducing blood levels of $CoQ_{10}$.

EXAMPLE 2

Case Summaries and Data

The present example presents 5 case studies wherein levels of coenzyme $Q_{10}$ were monitored both before and after administration of an HMG-CoA reductase inhibitor. In these studies, the particular HMG-CoA reductase inhibitor lovastatin (MEVACOR ®) was administered to the patients. The present example is also provided to demonstrate the utility of employing coenzyme $Q_{10}$ along with virtually any HMG-CoA reductase inhibitor treatment regimen to guard against depressed coenzyme $Q_{10}$-related cardiac dysfunction in a patient.

1. Case Data of Patient H.V.

Patient H.V., 55 years, was a white male with ischemic cardiomyopathy, and in Class III by the New York Heart Association.

The patient was orally treated with 100 mg of coenzyme $Q_{10}$ daily beginning in May, 1984. The patient's control blood level of $CoQ_{10}$ was 0.67 $\mu g/ml$ and his control ejection fraction (E.F.) was 60%. One month later (6/84), the $CoQ_{10}$ blood level had increased to 1.73 $\mu g/ml$ and the ejection fraction had increased to 75%. The following data on blood levels of $CoQ_{10}$ and on the ejection fractions (e.f.) from 7/84 to 9/87, show that oral and daily therapy with $CoQ_{10}$ of 1.73–2.78 $\mu g/ml$ provided ejection fractions of 64–70%.

During these three years of therapy with $CoQ_{10}$, the classification of ischemic cardiomyopathy of this patient had decreased from Class III to Class II and the quality of life of this patient was correspondingly significantly improved. On 9/87, this patient was treated with 40 mg of lovastatin (MEVACOR ®) daily and by 3/88 the patient had steadily deteriorated from a livable Class II to near Class IV which is known to be life-threatening. In this deterioration, the patient exhibited clinical decompensation and chest pain and required surgical revision of one graft.

Documenting the clinical deterioration, the patient's $CoQ_{10}$ blood level was 2.52 $\mu g/ml$ on 9/87 when treatment with lovastatin was initiated. About six months later on 3/88 his blood $CoQ_{10}$ level had diminished to 1.5 $\mu g/ml$ and to the very low level of 0.64 $\mu g/ml$ five months later on 8/88. On this later date, the ejection fraction had diminished to 54%. During the surgical period, it was not feasible to orally administer $CoQ_{10}$ for three weeks, but administration of $CoQ_{10}$ was resumed at 1.66 $\mu g/ml$ on 4/89. The administration of lovastatin was reduced from 40 mg per day to 20 mg per day on 11/88. The depressed $CoQ_{10}$ blood levels from the administration of lovastatin, which in conjunction with the reduction of the dosage of lovastatin from 40 mg to 20 mg daily and an increase in the dosage of $CoQ_{10}$ allowed the cardiac stabilization of this patient with acceptable blood levels of $CoQ_{10}$ allowed the cardiac stabilization of this patient with acceptable blood levels of $CoQ_{10}$ and that of the ejection fractions.

| CASE SUMMARY ON PATIENT H.V. | | | | | | | | |
|---|---|---|---|---|---|---|---|---|
| 1) H.V. 55 W/M Ischemic Cardiomyopathy. Class III to Class II. | | | | | | | | |
| Date | 5/84 | 6/84 | 7/84 | 10/84 | 5/85 | 11/85 | 5/86 | 9/86 |
| $\mu g/ml$ CoQ$_{10}$ | 0.67 | 1.73 | 1.32 | 1.81 | 2.41 | 2.13 | 2.57 | 2.12 |

-continued
CASE SUMMARY ON PATIENT H.V.

| | e.f. | 60 | 74 | 69 | 66 | 70 | 64 | 68 | 72 |
|---|---|---|---|---|---|---|---|---|---|
| | Date | 3/87 | 9/87 | 3/88 | 8/88 | 9/88 | 11/88 | 4/89 | |
| μg/ml | CoQ10 | 2.78 | 2.52 | 1.15 | 0.64 | 1.39 | 1.55 | 1.66 | |
| | e.f.++ | 70 | 70* | 76** | 54*** | 63 | 74**** | 71 | |

*lovastatin 40 mgm/day added.
**Patient rapidly deteriorated from Class II to near Class IV with decompensation and chest pain. Had surgical revision of one graft. Missed 3 weeks of CoQ10 during surgical period.
***CoQ10 resumed at 166 mgm/day
****lovastatin reduced to 20 mgm daily
++ ejection fraction Patient H.V. demonstrated blood levels of CoQ10 of 2.57–2.52 μg/ml between 5/86 and 9/87 on treatment with 100 mg of CoQ10 orally and daily. Ejection fractions of 68–70 were recorded during this same period. After initiating treatment with lovastatin (MEVACOR®) on 9/87, the blood level of CoQ10 declined within 6 months from 2.52 to 1.15 μg/ml, and then in five more months declined to 0.64 μg/ml. On this latter date, a dosage of CoQ10 was resumed at 166 mg/day and blood levels of CoQ10 increased to 1.39–1.66 μg/ml between 9/88 and 4/89. CoQ10 levels noticeably never reached levels of 2.5 μg/ml.

Although the dosage of lovastatin (mevinolin) was reduced on 11/88 from 40 to 20 mg daily, the blood levels of CoQ10 and the level of the ejection fraction remained essentially unchanged.

Clearly, the administration of lovastatin over time significantly reduced blood levels of CoQ10 and reduced the pumping of blood by the heart as monitored by the ejection fraction.

2. Case Data of Patient B.C.

Patient B.C. was a white male of 46 years of age with dilated cardiomyopathy. He was in Class III by the New York Heart Association and his control blood level of CoQ10 was 0.78 μg/ml and his control ejection fraction was 62% on 10/84. According to the following data, his blood levels of CoQ10 increased to the range of 1.79–2.31 μg/ml and his ejection fraction increased to the range of 68–71%. During this two-year and four-month period, his cardiac function and his quality of life had improved from Class III to Class I and his cardiac function stabilized at a clinically reasonably level.

The patient was given 20 mg daily of lovastatin. After 6–18 months later, patient CoQ10 blood levels had steadily declined from 2.29 to 1.82 to 1.50 to 1.12 μg/ml. On 10/88, the administration of lovastatin was terminated, and on 3/89 the patient's CoQ10 blood level had increased to 1.87 μg/ml.

CASE SUMMARY ON PATIENT B.C.
Patient B.C.
46 W/M Dilated Cardiomyopathy 51. Class II to Class I.

| Date | 10/84 | 12/84 | 3/85 | 9/85 | 3/86 | 10/86 | 4/87 | 10/87 | 4/88 | 10/88 | 3/89 | |
|---|---|---|---|---|---|---|---|---|---|---|---|---|
| CoQ10 | 0.78 | | 1.96 | 1.79 | 2.31 | 2.09 | 1.86 | 2.29 | 1.82 | 1.50 | 1.12 | 1.87 |
| E.F. | 62 | 69 | 70 | 71 | 71 | 71 | 68* | 70 | 68 | 71** | 63 | |

*lovastatin 20 mgm/day
**lovastatin stopped

These data on patient B.C. clearly show reduction of blood levels of CoQ10 over time from the administration of lovastatin and the increase in blood levels of CoQ10 when the administration of lovastatin was terminated.

3. Case Data on Patient S.F.

Patient S.F. was a white female of 43 years (now 46) and had dilated cardiomyopathy. This patient was classified in severe Class IV when treatment with CoQ10 was initiated.

Between 3/86 and 9/87, her blood CoQ10 levels ranged from 1.68–3.22 μg/ml and her ejection fraction ranged from 52–60%. Her clinical status improved to Class III.

On 9/87, treatment with 20 mg of lovastatin was initiated. By 3/88, the patient's cardiac condition had significantly deteriorated to a severe Class IV, and the patient was referred for a heart transplant.

On 3/88, the patient's dosage of CoQ10 was increased to 200 mg/daily. Blood levels of CoQ10 increased to the range of 4.24–5.43 between 10/88 and 4/89, and on this later date, the patient's cardiac condition had significantly improved from Class IV to Class III, which is explained on the basis of the increase in the daily dosage of CoQ10 to 200 mg daily and in the presence of continuing daily treatment of 20 mg of lovastatin.

CASE SUMMARY ON PATIENT S.F.
S.F. 26 W/F Dilate Cardiomyopathy. Class IV - Class III.

| Date | 3/86 | 9/86 | 3/87 | 9/87 | 3/88 | 10/88 | 4/89 |
|---|---|---|---|---|---|---|---|
| CoQ10 | 1.68 | 3.25 | 4.26 | 3.22 | 2.57 | 4.24 | 5.43 |
| e.f. | 52 | 55 | 54 | 60* | 48** | 66*** | 75**** |

*lovastatin 20 mgm added
**Rapid deterioration to severe Class IV. Referred for transplant. CoQ10 increased to 200 mgm/day.
***CoQ10 increased to 166 mgm/day
****Improved to Class III The patient was initially in Class IV and her cardiomyopathy improved to Class III after treatment with COQ10. After treatment with lovastatin was added, the patient deteriorated from Class III to severe Class IV and so rapidly that she was referred for a cardiac transplant. The patient's dosage of CoQ10 was then increased from 100 to 200 mg daily, and resulted in improved ejection fraction and reclassification to Class III.

Case Data on Patient M.O.

Patient M.O. was a 72-year old white female in Class III with dilated cardiomyopathy.

On 3/86, the patient's blood level of CoQ10 was 0.79 μg/ml and her ejection fraction was 58%. On 100 mg of CoQ10 daily, her CoQ10 blood level after 3 months was 1.21 μg/ml and ejection fraction remained at 58%. On 9/86, the CoQ$_{10}$ dosage was increased to 133 mg daily and during 3/87-9/87 her CoQ$_{10}$ blood levels were 1.70 and 2.23 µg/ml with an improved ejection fraction of 61-63%.

On 9/87, the administration of lovastatin was initiated at 20 mg daily and by 3/88 the CoQ$_{10}$ blood level had decreased to 0.99 µg/ml and ejection fraction was 65%. on 8.88, her blood level of CoQ$_{10}$ was 1.68 µg/ml and on 2/89, it was 1.00 µg/ml. On the higher dosage of CoQ$_{10}$ her ejection fraction ranged from 76-79%.

Again, the administration of lovastatin had decreased the blood level of CoQ$_{10}$ during six months.

| CASE SUMMARY OF M.O. | | | | | | | |
|---|---|---|---|---|---|---|---|
| M.O. | 72 W/F Dilated Cardiomyopathy. Class III to Class II. | | | | | | |
| Date | 3/86 | 6/86 | 9/86 | 3/87 | 9/87 | 3/88 | 8/88 | 2/89 |
| CoQ$_{10}$ | 0.79 | 1.21 | 1.21 | 1.70 | 2.23 | 0.99 | 1.68 | 1.00 |
| e.f. | 58 | 58 | 64* | 63 | 61 | 65 | 76 | 79*** |

*CoQ$_{10}$ increased to 133 mgm/day
**lovastatin 40 mgm/day
***CoQ$_{10}$ increased to 166 mgm/day When this 72-year old female with Class III cardiomyopathy was treated with CoQ$_{10}$, her cardiomyopathy improved to Class II in 12 months. On administration of lovastatin, her CoQ$_{10}$ blood level significantly diminished and with deterioration in clinical status but not in ejection fraction.

5. Case Data on Patient J.G.

Patient J.G. was a 66-year old white male with ischemic cardiomyopathy and who was initially in Class I when lovastatin at a daily dosage of 20 mg was initiated. On that date, 1.88 the ejection fraction was 85%. one year later, the blood level of CoQ$_{10}$ was 0.61 µg/ml and the ejection fraction had decreased to 52% at which time 100 mg of CoQ$_{10}$ daily was initiated because the cardiomyopathy had definitely worsened to Class III. By 3/89, the CoQ$_{10}$ level was 1.02 µg/ml and the ejection fraction was 61% and the dosage of CoQ$_{10}$ was increased to 133 mg daily.

For this patient, J.G., lovastatin (mevinolin) significantly decreased the ejection fraction over a year and increased the severity of ischemic cardiomyopathy from Class I to Class III. The administration of CoQ$_{10}$ had increased within two months the blood CoQ$_{10}$ level to offset the depression of this blood level from lovastatin.

| CASE SUMMARY ON J.G. | | | | |
|---|---|---|---|---|
| J.G. | 67 W/M Ischemic Cardiomyopathy. Class I-III | | | |
| Date | 1/88 | 1/89 | 3/89 | 6/89 |
| Coq$_{10}$ | — | 0.61 | 1.02 | 1.01 |
| e.f. | 85* | 52** | 61*** | 66 |

*lovastatin 20 mgm/day
**CoQ$_{10}$ 100 mgm/day
***CoQ$_{10}$ 133 mgm/day

Patient J.G., 67 yrs, was post-op bypass because of ischemic heart disease in Class I. He was placed on lovastatin on 5/88 because of elevated blood lipids. However, there was progressive symptoms of weakness and dyspnea on activities and his cardiac status had declined from Class I to Class III by 1/89 with a corresponding decrease in ejection fraction. When CoQ$_{10}$ was given at 100 mg daily, his CoQ$_{10}$ blood level increased from 0.61 to 1.02 µg/ml and his ejection fraction increased from 52 to 61%, on 1/89 and 3/89, respectively. When his CoQ$_{10}$ dosage was increased from 100 to 133 mg daily on 3/89, the ejection fraction increased to 66% by 6/89.

Patients B.C. and M.O. revealed quite rapid cardiovascular deterioration on lovastatin. This deterioration was sufficiently progressive and severe that neither patient was expected to live very long. For both of these patients, their clinical course was significantly improved when the dosage of CoQ$_{10}$ was increased.

EXAMPLE 3

Therapy of Cardiomyopathy With Coenzyme Q$_{10}$ in the Absence of an HMG-CoA Reductase Inhibitor Lovastatin The present example is provided to demonstrate the utility of employing coenzyme Q$_{10}$, without an HMG-CoA reductase inhibitor for the treatment of cardiomyopathy in a patient.

Langsjoen et al.[11] reported in 1988 on the effective and safe therapy with coenzyme Q$_{10}$ for cardiomyopathy. Patients with the lowest ejection fractions (approximately 10-30%) showed the highest increases (115Δ%-210Δ%) and those with higher ejection fractions (50%-80%) showed increases of approximately 10Δ%-25Δ%) on therapy. By functional classification, 17/21 in Class IV, 52/62 in Class III and 4/5 in Class II improved to lower Classes. Clinical responses were variable and were presumed to be based on mechanisms of DNA-RNA protein synthesis of apoenzymes which restored levels of CoQ$_{10}$ enzymes in a deficiency state. 10/21 (48%) of patients in Class IV, 26/62 (42%) in Class III, and 2/5 (40%) in Class II had exceptionally low control blood levels of CoQ$_{10}$. Clinical responses on therapy with CoQ$_{10}$ appear maximal with blood levels of approximately 2.5 µg/ml and higher during therapy.

The administration of lovastatin to such patients with cardiomyopathy which depressed blood levels of CoQ$_{10}$ would definitely be deleterious to cardiac function, and would be increasingly life-threatening in relationship to the increasing severity of the cardiac disease.

Langsjoen et al.[12] summarized the long-term efficacy and safety of coenzyme Q$_{10}$ to treat cardiomyopathy. Their study involved the administration of doses of 100 mg of CoQ$_{10}$ daily to 143 patients with cardiomyopathy for up to six years for up to a total of 402 patient years of exposure. The generally low control blood levels of CoQ$_{10}$ were corrected well into the normal range and remained stable thereafter. Myocardial contractility, as measured by ejection fraction, was significantly improved in 85% of all patients and this improvement was sustained for up to six years and correlated well with improvement in the quality of life. Clinical improvements of 1 or 2 NYHA Classes were recorded in 85% of all cases. Survival figures were highly encouraging. CoQ$_{10}$ was proven efficacious and safe for the treatment of cardiomyopathy over a six-year period. It was evident that abnormalities in intracellular bioenergetics are likely factors in the enigma of myocardial failure and present the unique medical opportunity to correct his serious health problem from an entirely new biochemical approach. In this study, over six years, there were no significant side reactions.

It is discovered from the data herein that the administration of HMG-CoA reductase inhibitor, such as lovastatin, to patients having from mild to severe cardiomyopathy depresses CoQ$_{10}$ blood levels, and is definitely deleterious to cardiac function, and may be life-threatening.

EXAMPLE 4

Coenzyme Q$_{10}$ and the HMG-CoA Reductase Inhibitor Pravastatin

The present example is provided to demonstrate the utility using the HMG-CoA reductase inhibitor, pravastatin in conjunction with coenzyme Q$_{10}$ to preserve Coenzyme Q$_{10}$ levels in vivo. As such, the present example is also submitted to demonstrate the utility and advantage of employing CoQ$_{10}$ with another HMG-CoA reductase inhibitor, in vivo to prevent HMG-CoA reductase inhibitor-related side effects linked to depressed physiological levels of coenzyme Q$_{10}$. Exposure to HMG-CoA reductase inhibitor pravastatin result in lowered coenzyme Q$_{10}$ levels. By preserving and enhancing levels of physiological CoQ$_{10}$, side effects linked to lowered CoQ$_{10}$ levels may be inhibited if not eliminated altogether.

The present example also provides a comparison of the effects of pravastatin and lovastatin on coenzyme Q$_{10}$ levels in rats. Additionally, the effects of lovastatin on liver are also revealed.

A total of 9 Sprague-Dawly adult male rats were employed in the present example. Control rats were fed ground laboratory chow (N=3). A second group of 3 rats were fed ground laboratory chow containing lovastatin at 400 mg/kg of diet. A third group of 3 rats were fed ground laboratory chow containing pravastatin at 400 mg/kg of diet.

One rat from each group was sacrificed at two weeks, at four weeks, and at eight weeks from the start of the project. Blood and heart tissues were analyzed for Coenzyme Q$_{10}$ concentrations. Liver was analyzed for lipid content. Additionally, livers were examined histologically via both light and electron microscopy.

The results, provided at Table 2, are consistent with the biochemistry that inhibition of HMG-CoA reductase through administration of an HMG-CoA reductase inhibitor, will result in a lowering of serum Coenzyme Q$_{10}$ concentrations in vivo.

TABLE 2

Study of Lovastatin and Pravastatin on Coenzyme Q$_{10}$ Serum Concentration

| Group (N = 3) | Heart (CoQ$_{10}$) | Blood |
|---|---|---|
| Control (lab chow) | 0.14 ± 0.015 | 0.21 ± 0.029 |
| Lovastatin (lab chow + 400 mg/kg lovastatin) | 0.10 ± 0.010 | 0.18 ± 0.025 |
| Pravastatin (lab chow + 400 mg/kg pravastatin) | 0.11 ± 0.020 | 0.17 ± 0.015 |

The following references are especially incorporated herein in pertinent part for the purposes indicated.

Those of skill in the pharmaceutical and/or cardiovascular medical arts will be able to practice the present invention with the aid of the disclosure provided here, the following references may facilitate practice or enhanced understanding of certain aspects. Inclusion of a reference in this list is not intended to and does not constitute an admission that the reference constitutes prior art with respect to the present invention.

BIBLIOGRAPHY

1. Alberts et al. (1980), *Proc. Natl. Acad. Sci. USA*, 77(7):3957-3961.
2. Crane et al. (1986), *Biomedical and Clinical Aspects of Coenzyme Q*, Vol. 5, K. Folkers & Y. Yamamura, eds., Arasterdam, The Netherlands: Elsevier Science Publishers B.V.: pp. 3-14.
3. Enco et al. (1976), *F.E.B.S. Lett.*, 72:323-326.
4. U.S. Pat. No. 4,231,938
5. U.S. Pat. No. 4,444,784
6. U.S. Pat. No. 4,396,227
7. Goodman and Gilman, eds., In: *The Pharmacological Basis of Therapeutics*, 7th edition (1985), MacMillan Publishing Company, New York, NY, pp. 841-845.
8. Budavari et al., eds. (1989) In: *The Merck Index*, 11th edition, Merck & Co., Inc. Publishers, p. 1222.
9. U.S. Pat. No. 4,885,167—Folkers et al. (1989).
10. U.S. Pat. No. 4,824,669—Folkers et al. (1989).
11. Langsjoen et al. (1988), Klinische Wochenschrift, 66:583-590.
12. Langsjoen et al. (1989), *The American Journal of Cardiology*.
13. Balasubramanian, N., et al. (1989), *J. Med. Chem.*, 32, 2038-2041.
14. Roth, B.D. et al. (1991), *J. Med. Chem.*, 34, 357-366.
15. Krause, R. et al. (1990), *J. Drug Dev.*, 3 (Suppl. 1), 255-257.
16. Karanewsky, D.S. et al. (1990), *J. Med. Chem.*, 33, 2952-2956.
17. Folkers et al. (1985), PNAS, 82:901.

Changes may be made in formulations of HMG-CoA reductase inhibitors and of coenzyme Q$_{10}$, and changes may be made in the dosage schedule of formulations and of the various elements, and changes may be made in the steps and procedures described herein without departing from the concept and scope of the invention as defined in the following claims.

What is claimed:

1. A method for ameliorating reductions of coenzyme Q$_{10}$ in cardiomyopathy patients receiving an HMG-CoA reductase inhibitor comprising administering concurrently with said HMG-CoA reductase inhibitor coenzyme Q$_{10}$ at a concentration sufficient to raise serum levels of coenzyme Q$_{10}$ to at least 2.0 µg/ml.

2. The method of claim 1, wherein the HMG-CoA reductase inhibitor is selected from the group consisting of:
   lovastatin;
   pravastatin;
   simvastatin;
   fluvastatin;
   dalvastatin;
   compactin;
   HR-780;
   B My 22,089;
   B My 22,566;
   SQ 33,600;
   GR 95,030; or
   CI 981.

3. The method of claim 1 wherein the HMG-CoA reductase inhibitor is pravastatin.

4. The method of claim 1 wherein the concentration of coenzyme Q$_{10}$ sufficient to raise serum levels of coenzyme Q$_{10}$ to at least 2.0 µg/ml is at least 200 mg/day for at least 30 days.

* * * * *